(12) United States Patent
Kerber

(10) Patent No.: US 10,602,964 B2
(45) Date of Patent: Mar. 31, 2020

(54) LOCATION, ACTIVITY, AND HEALTH COMPLIANCE MONITORING USING MULTIDIMENSIONAL CONTEXT ANALYSIS

(71) Applicant: KONINKLIJKE PHILIPS N.V., Eindhoven (NL)

(72) Inventor: Cameron Lee Kerber, Sykesville, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 216 days.

(21) Appl. No.: 15/649,725

(22) Filed: Jul. 14, 2017

(65) Prior Publication Data
US 2018/0049675 A1 Feb. 22, 2018

Related U.S. Application Data

(60) Provisional application No. 62/376,139, filed on Aug. 17, 2016.

(51) Int. Cl.
*A61B 5/00* (2006.01)
*A61B 5/11* (2006.01)
(Continued)

(52) U.S. Cl.
CPC .......... *A61B 5/1112* (2013.01); *A61B 5/0022* (2013.01); *A61B 5/0205* (2013.01); *A61B 5/1118* (2013.01); *A61B 5/68* (2013.01); *A61B 5/7465* (2013.01); *G06F 19/3418* (2013.01); *G16H 10/60* (2018.01); *G16H 20/30* (2018.01); *G16H 40/67* (2018.01); *G16H 50/20* (2018.01); *G16H 50/30* (2018.01)

(58) Field of Classification Search
CPC combination set(s) only.
See application file for complete search history.

(56) References Cited

U.S. PATENT DOCUMENTS 5,396,886 A * 3/1995 Cuypers ............... A61B 5/0205
600/301
5,692,501 A * 12/1997 Minturn ................ A61B 5/00
600/301

(Continued)

OTHER PUBLICATIONS

"Doctor's Orders: Mobile Solutions for Medication Therapy Management" by T. Holland, c. 1995-2016 (https://insights.samsung.com/2016/01/21/doctorsorders-mobile-solutions-for-medication-therapy-management/).

(Continued)

*Primary Examiner* — Michael W Kahelin
*Assistant Examiner* — Shirley X Jian

(57) ABSTRACT

A system and method for monitoring patient activity, location, present health status, and health protocol compliance. The present invention provides a more complete and accurate picture of a patient's health and safety context through a multi-dimensional user health and safety context analysis. Based on the combined computed health compliance score, calculated activity index, the computed location score, and calculated user health index, an overall user health and safety score is calculated. If the computed overall user health and safety score violates a predefined threshold or threshold range, an alert is transmitted to one or more persons.

18 Claims, 6 Drawing Sheets

(51) Int. Cl.
    *G06F 19/00*     (2018.01)
    *A61B 5/0205*     (2006.01)
    *G16H 40/67*     (2018.01)
    *G16H 50/30*     (2018.01)
    *G16H 50/20*     (2018.01)
    *G16H 10/60*     (2018.01)
    *G16H 20/30*     (2018.01)

(56) References Cited

U.S. PATENT DOCUMENTS

| | | | |
|---|---|---|---|
| 6,576,471 B2 * | 6/2003 | Otvos | G01N 33/92 436/71 |
| 7,945,451 B2 * | 5/2011 | Cosentino | G06F 19/3418 705/2 |
| 8,092,380 B2 * | 1/2012 | Rothman | G06F 19/322 600/300 |
| 8,241,213 B2 * | 8/2012 | Lynn | A61B 5/00 600/301 |
| 8,768,718 B2 * | 7/2014 | Cazares | G06Q 50/22 705/2 |
| 9,081,879 B2 * | 7/2015 | Iliff | G06Q 50/22 |
| 2006/0030890 A1 * | 2/2006 | Cosentino | A61B 5/00 607/5 |
| 2007/0232454 A1 * | 10/2007 | Kagan | A61B 5/024 482/8 |
| 2008/0157980 A1 * | 7/2008 | Sachanandani | A61B 5/0031 340/573.1 |
| 2008/0162182 A1 * | 7/2008 | Cazares | G06Q 50/22 705/2 |
| 2009/0048493 A1 * | 2/2009 | James | G06F 19/3481 600/300 |
| 2009/0171939 A1 * | 7/2009 | Athsani | G06F 16/29 |
| 2009/0177068 A1 | 7/2009 | Stivoric et al. | |
| 2010/0022848 A1 * | 1/2010 | Lee | A61B 5/0002 600/300 |
| 2010/0056872 A1 * | 3/2010 | Kahn | A61B 5/1038 600/300 |
| 2010/0062818 A1 * | 3/2010 | Haughay, Jr. | A63B 24/0062 463/7 |
| 2013/0116578 A1 * | 5/2013 | An | A61B 5/0205 600/484 |
| 2013/0158367 A1 * | 6/2013 | Pacione | A61B 5/0022 600/301 |
| 2014/0077946 A1 | 3/2014 | Tran | |
| 2014/0107493 A1 * | 4/2014 | Yuen | A61B 5/0205 600/473 |
| 2015/0112158 A1 * | 4/2015 | He | A61B 5/0285 600/301 |
| 2015/0324751 A1 * | 11/2015 | Orenstein | G06F 19/3481 702/3 |
| 2015/0347599 A1 * | 12/2015 | McMains | G16H 10/60 707/723 |
| 2016/0157735 A1 * | 6/2016 | Zhang | A61B 5/02055 600/301 |
| 2016/0161985 A1 * | 6/2016 | Zhang | G06F 1/163 361/679.03 |
| 2016/0263435 A1 * | 9/2016 | Venkatraman | G01S 19/13 |
| 2016/0328991 A1 * | 11/2016 | Simpson | A61B 5/742 |
| 2018/0189913 A1 * | 7/2018 | Knopp | H04W 4/90 |
| 2018/0247713 A1 * | 8/2018 | Rothman | G16H 40/67 |

OTHER PUBLICATIONS

Vashist, S. K., et al. "Commercial smartphone-based devices and smart applications for personalized healthcare monitoring and management," Diagnostics 4, No. 3 (2014): 104-128.

* cited by examiner

LOCATION, ACTIVITY, AND HEALTH COMPLIANCE MONITORING USING MULTIDIMENSIONAL CONTEXT ANALYSIS

CROSS REFERENCED APPLICATIONS

This application claims the benefit of U.S. Provisional Application No. 62/376,139, filed on 17 Aug. 2016. This application is hereby incorporated by reference herein.

BACKGROUND OF THE INVENTION

Conventional patient and elderly monitoring systems and methods typically involve tracking their location and monitoring either a patient's medical compliance or a patient's one or more physiological parameters. These monitoring systems or methods, however, do not provide medical personnel, for example, who normally need to attend to many patients on the same day, with a relatively complete and accurate picture regarding a patient's health and safety at a given time and place. Typically, a patient's health and safety context requires more than just two parameters to determine whether a patient or an elderly resident really needs immediate assistance in one form or another. Thus, the greater the number of data types fed into a monitoring system, the less chances that false alarms will be generated. False alarms are costly in terms of the time, money, and emotional distress and uncertainty they bring to family members, especially when a family has to constantly deal with other family members such as very young children or other sick relatives.

The online article "Doctor's Orders: Mobile Solutions for Medication Therapy Management" by T. Holland, c. 1995-2016 (https://insights.samsung.com/2016/01/21/doctors-orders-mobile-solutions-for-medication-therapy-management/) discloses a medication dispenser and communication hub that provides geofencing and alert capabilities and connection to various medical devices such as blood pressure cuffs and pulse oximeters. US Patent Application No. 20140077946 discloses a wearable device that can be used to monitor a patient's location and as part of a mesh network for monitoring patient compliance. The journal article *Diagnostics* 2014, vol. 4, No. 3, pp. 104-128 discloses radar responsive tags with smart diagnostic skin patches for use in patient location and physiological parameter monitoring.

BRIEF SUMMARY OF THE INVENTION

The present invention generally relates to a method for monitoring patient activity, location, present health status, and health protocol compliance. In particular, the present invention provides a more complete and accurate picture of the user's health and safety context through a multi-dimensional user health and safety context analysis. In a preferred embodiment, the multi-dimensional user health and safety context analysis is a weighted multi-dimensional user health and safety context analysis. In another preferred embodiment, the method of the present invention further comprises using a learning algorithm to further enhance the accuracy and reliability of the overall user context analysis.

The method of the present invention comprises acquiring one ore more of the following user information: the user's most-recently assigned health protocol, historical activity and medical records, frequently-visited places, user's current location, and one or more scheduled activities from a user's personal record. The patient undergoes monitoring via an at least one monitoring device to determine at least the user compliance to the acquired user's most-recently assigned health protocol. Based on the determined patient compliance, an at least one compliance score is computed.

The present invention further comprise computing a user location score calculated using at least one of current user location, historical activity record, frequently-visited places, and one or more scheduled user activities. In addition, the present invention comprises calculating a user activity score based on at least one of the user's historical activity record, medical record, frequently-visited places, user's current location, and one or more scheduled user activities.

A user health index is also calculated based on measured one or more physiological parameters and comparison with corresponding one or more preset physiological parameter thresholds. Based on the combined computed health compliance score, calculated activity index, the computed location score, and calculated user health index, an overall user health and safety score is calculated. If the computed overall user health and safety score exceeds or lies outside a predefined threshold or threshold range, an alert is transmitted to one or more persons, e.g., a family member or medical personnel.

BRIEF DESCRIPTION OF THE DRAWINGS

The accompanying drawings, which are included to provide a further understanding of the invention, are incorporated herein to illustrate embodiments of the invention. Along with the description, they also serve to explain the principle of the invention. In the drawings.

DETAILED DESCRIPTION OF THE VARIOUS EMBODIMENTS OF THE INVENTION

Figure 1A:
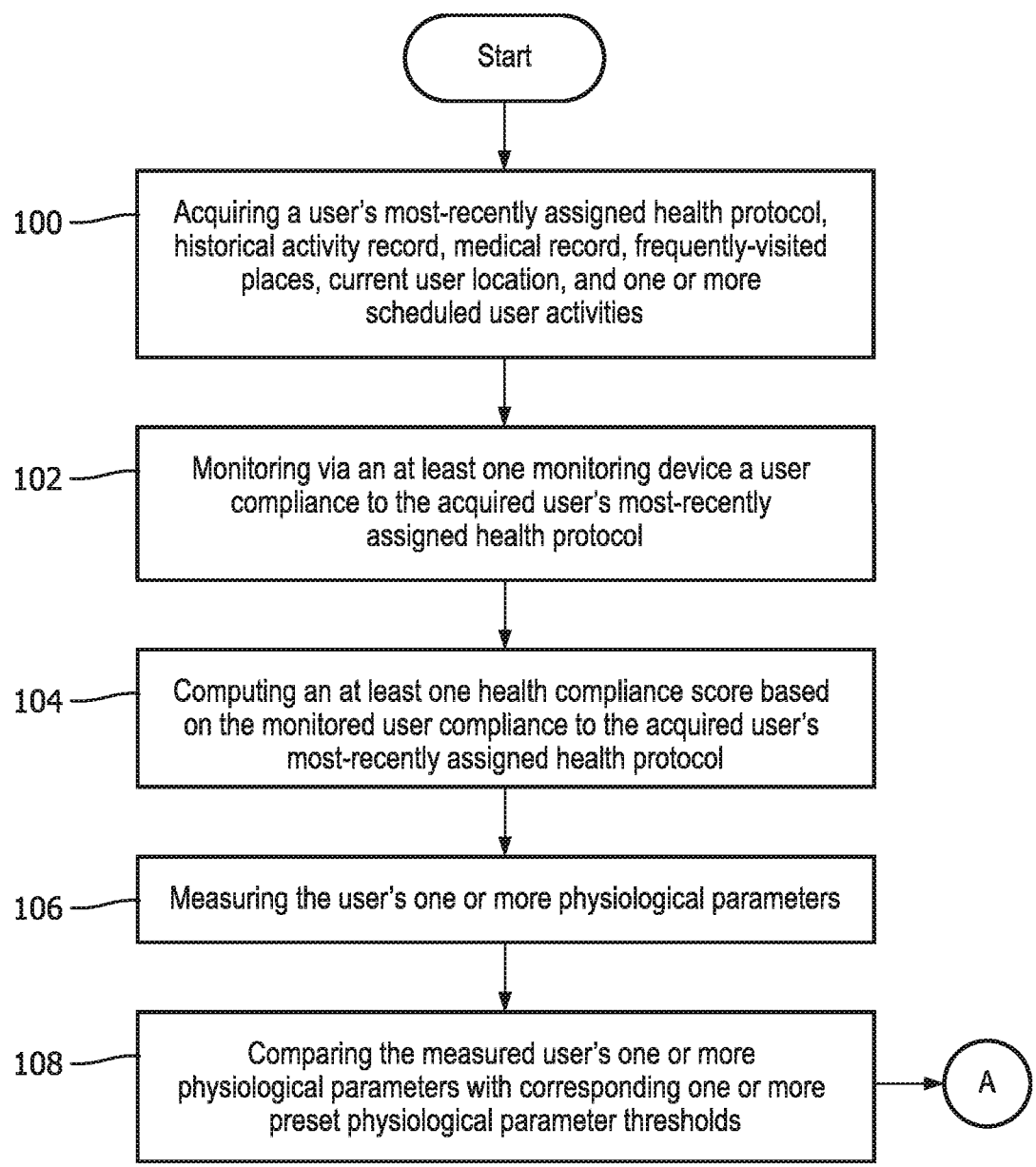
FIG. 1A and FIG. 1B are flowcharts illustrating a preferred embodiment of the method of the present invention.

The present invention is directed to a method of user health and safety monitoring based on a multi-dimensional user health and safety context analysis. In a preferred embodiment of the present invention, the user health and safety context analysis is a weighted multi-dimensional context analysis. The method of the present invention comprises: acquiring a user's most-recently assigned health protocol, historical activity record, medical record, frequently-visited places, current user location, and one or more scheduled user activities; monitoring via an at least one monitoring device a user compliance to the acquired user's most-recently assigned health protocol; computing an at least one health compliance score based on the monitored user compliance to the acquired user's most-recently assigned health protocol; measuring the user's one or more physiological parameters; comparing the measured user's one or more physiological parameters with corresponding one or more preset physiological parameter thresholds; calculating a user health index based on the measured one or more physiological parameters and comparison with the corresponding one or more preset physiological parameter thresholds.

The present invention also comprises computing a location score calculated using at least one of the acquired current user location, historical activity record, frequently-visited places, and one or more scheduled user activities; and calculating a user activity score based on at least one of the user's historical activity record, medical record, frequently-visited places, user's current location, and one or more scheduled user activities.

The present invention further comprises computing an overall user health and safety score based on the computed health compliance score, calculated user health index, calculated activity score, and the computed location score; and sending an alert when the computed overall user health and safety score exceeds a predefined threshold.

The calculation of these scores involves not just a straightforward binary determination of whether or not a patient has taken his or her medication, whether or not a patient is in a particular location, or whether or not the patient performed an activity prescribed by the patient's primary physician. For example, the calculation of the health compliance score preferably additionally takes into account other parameters that includes a patient's age, known level of cognitive, motor and coordination skills, pre-existing medical conditions, latest medical diagnosis, prohibited activities based on known one or more medical conditions, required or typical rest schedules or sleeping times, required physical exercises or schedule of sessions with a physical therapist or trainer, scheduled hospital or doctor visitations, etc. Each of these parameters are assigned an appropriate score, which depending on the parameter type, may be a binary 1 or 0 score, or based on a scale such as 0-5 with 5 corresponding to very important and 0 being not required. In another embodiment, a score may assume or be assigned a negative value in cases where the detected patient activity or location, for example, is prohibited, not recommended, or previously determined to be unsafe. Under this scoring scheme, the lower the overall health and safety score is, the more likely that an alert is going to be issued (e.g., when the calculated total score exceeds or goes below a preset threshold) based on a predicted unsafe patient situation or predicament.

The location-based score, on the other hand, is based on, for example, whether a patient or user being tracked is in a location deemed unsafe or safe. In a preferred embodiment, all locations, facilities, residences, buildings (e.g., church, grocery stores, friends' houses, gym, clinic, hospital, barber shop, movie houses, etc.) that a patient frequently or regularly visits or is expected to visit, and all other nearby places or locations that are accessible to the patient, whether deemed safe or unsafe for the patient, are initially inputted into the monitoring system's locations database. Preferably, each of those entered location is assigned an initial default score (e.g., "+1" for the church or barber shop within the neighborhood or "−1" for the deep lake a few miles away from the patient's home). The initial default score assigned to any of the recorded locations may later be modified if, for example, the location's safety classification has changed (e.g., from unsafe to safe). In one embodiment, a previously unvisited, unrecorded, or unclassified patient location inputted later into the locations database is initially assigned a score of "0" (zero) until verified to be safe or unsafe.

The overall location score preferably includes the case in which the patient moves from one location to at least one other location over a given period. Locations deemed safe may be assigned a positive score to indicate that the patient's location is relatively safe such as residences of family members and relatives, hospitals, clinics, church, schools, gyms, movie theaters, malls, and supermarkets. The overall score tracking can be performed intermittently, repeatedly based on a preset time interval, or continuously over a given period. Continuous monitoring may be preferable when the patient is being monitored, for example, after being discharged from a hospital after a major operation or procedure, or when the patient is undergoing medical observation for a still unverified but potentially serious medical condition.

Alternatively, geofencing could be used to assign a score to various regions on a map rather than score specific locations. In addition, it is also contemplated that the system could be adaptive and detect vital signs of a patient and adjust the location score based on the detected health parameters. In this way, new locations could be automatically scored without needing to manually determine its particular classification. Data may be shared across the entire patient population to populate these maps. For instance, if the patient typically has heightened blood pressure without a corresponding increase in respiration rate, that may be indicative of stress. Such a location may have its score decreased to indicate that it is a location that decreases health. By way of example, the location score could be decreased by 0.5 if it resulted in a modest increase in blood pressure, decreased by 1 if it resulted in a moderate increase in blood pressure and a 1.5 if it resulted in an extreme increase in blood pressure. Of course, other weightings could be contemplated without deviating from the scope of this invention.

The activity-based score is calculated according to, for example, whether a monitored patient is engaging in activities recommended by his or her primary physician, physical therapist, or fitness coach. Preferably, the activity-based score is calculated partly by comparing the detected or identified activity being performed by the patient with a previously scheduled list of activities for the day stored in a database or a handheld device. For example, if the patient was detected to be performing brisk walking on a treadmill in a gym, which matches one of the patient's scheduled activities for that day, then the present invention assigns a corresponding score for that particular activity for that day under an overall activity score. In one embodiment of the present invention, a lower score (or a higher score, depending on the scoring system used) is assigned if the patient is performing an activity other than a scheduled activity for that time or time interval of the day. For example, an activity score of "1" may be assigned in the case wherein the actual activity being performed by the patient matches that scheduled in the patient's calendar for that particular time of the day. If instead of a scheduled aerobic exercise session, the patient was determined by the system to be located in a library, the system may be set to assign a score of "0" inferring that the patient is likely to be in indulging in a leisure activity that is neither recommended nor prohibited for the patient. In a third case, the system may be preset to assign an activity score of "−1" if the patient was determined to be performing a prohibited activity, for example, the patient was running along a nature trail or a treadmill even though the patient's physician previously recommended that the patient avoid certain types of exercises such as running while the patient is still recovering from a previous knee injury.

After calculating the health compliance score, health index, activity-based score, and location-based score for a given patient or user, the combined score is compared with a preset threshold to determine whether an alert needs to be sent. Preferably, the monitoring system also determines based on the compared combined score at least whether the alert needs to be transmitted to relatives only or to both medical personnel and relatives. Preferably, the alert specifies both the specific condition and location of the patient that triggered the alert. In another preferred embodiment, an alert mode corresponding to a critical level medical or health alert also sounds off an audible alarm that people within the patient's vicinity could hear to notify them that the patient needs to be brought to the nearest medical facility. Preferably, the public alert includes an address or phone number to be called when a critical-level public alert is set off.

FIG. 1A is a flowchart illustrating a preferred embodiment of the method of the present invention. In the first step, the monitoring system acquires at least one of a user's most-recently assigned health protocol, historical activity record, medical record, frequently-visited places, current user location, and one or more scheduled user activities (step 100). After the initial data acquisition, the monitoring system performs monitoring via an at least one monitoring device a user compliance to the acquired user's most-recently assigned health protocol (step 102). An at least one health compliance score is then computed based on the monitored user compliance to the acquired user's most-recently assigned health protocol (step 104). The system also measures the user's one or more physiological parameters (step 106) and then compares the measured user's one or more physiological parameters with corresponding one or more preset physiological parameter thresholds (step 108).

Figure 1B:
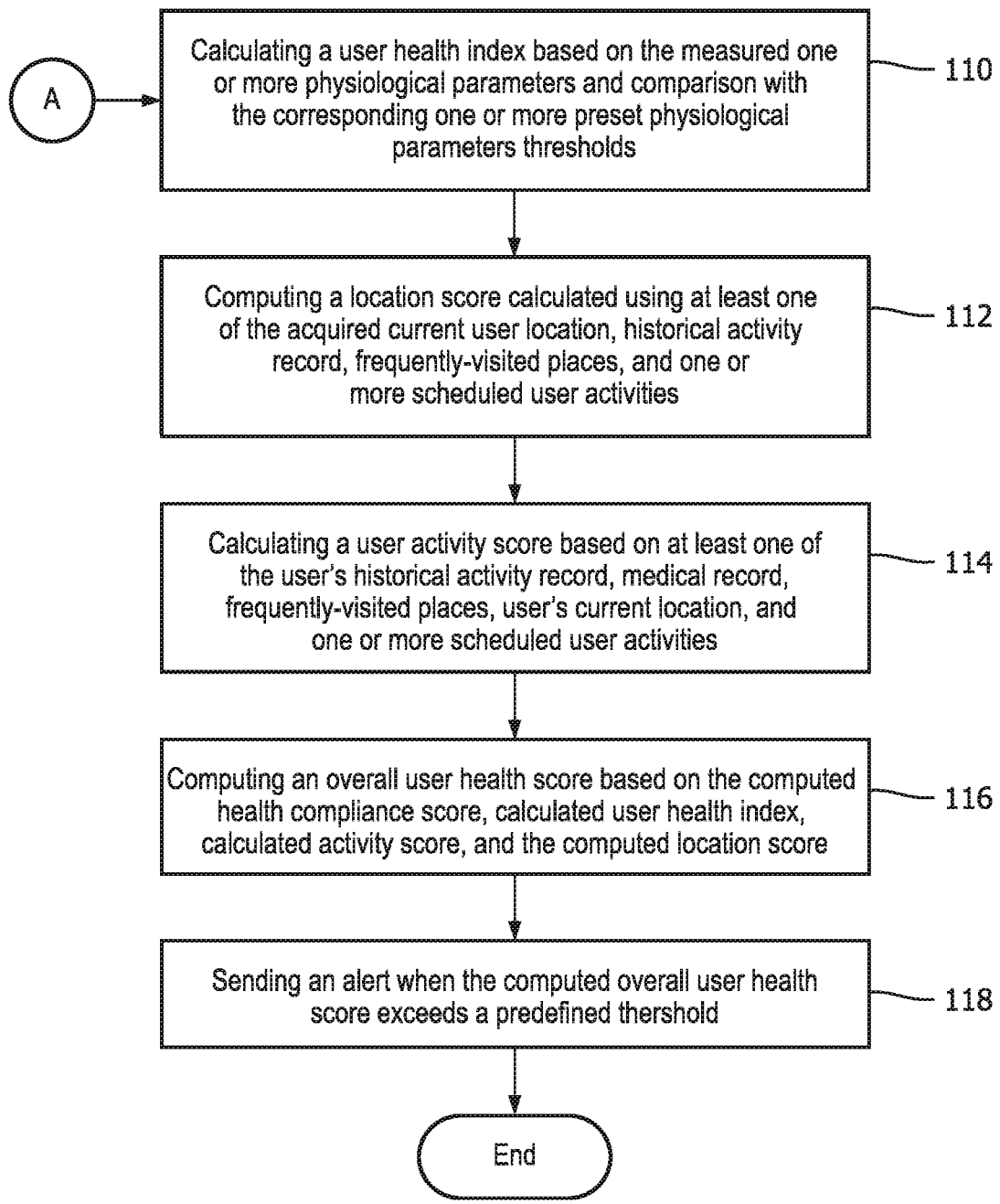

Continuing to FIG. 1B, the method of the present invention then proceeds to calculating a user health index based on the measured one or more physiological parameters and comparison with the corresponding one or more preset physiological parameter thresholds (step 110). Then a location score is calculated using at least one of the acquired current user location, historical activity record, frequently-visited places, and one or more scheduled user activities (step 112). After calculating a user location score, the system also calculates a user activity score based on at least one of the user's historical activity record, medical record, frequently-visited places, user's current location, and one or more scheduled user activities (step 114). After calculating the individual scores, an overall user health and safety score based on the computed health compliance score, calculated user health index, calculated activity score, and the computed location score is calculated (step 116). If the computed overall user health and safety score exceeds (or falls below, depending on the scoring scheme adopted) a predefined threshold, the monitoring system will send an alert to one or more contact persons or locations (step 118).

Figure 2:
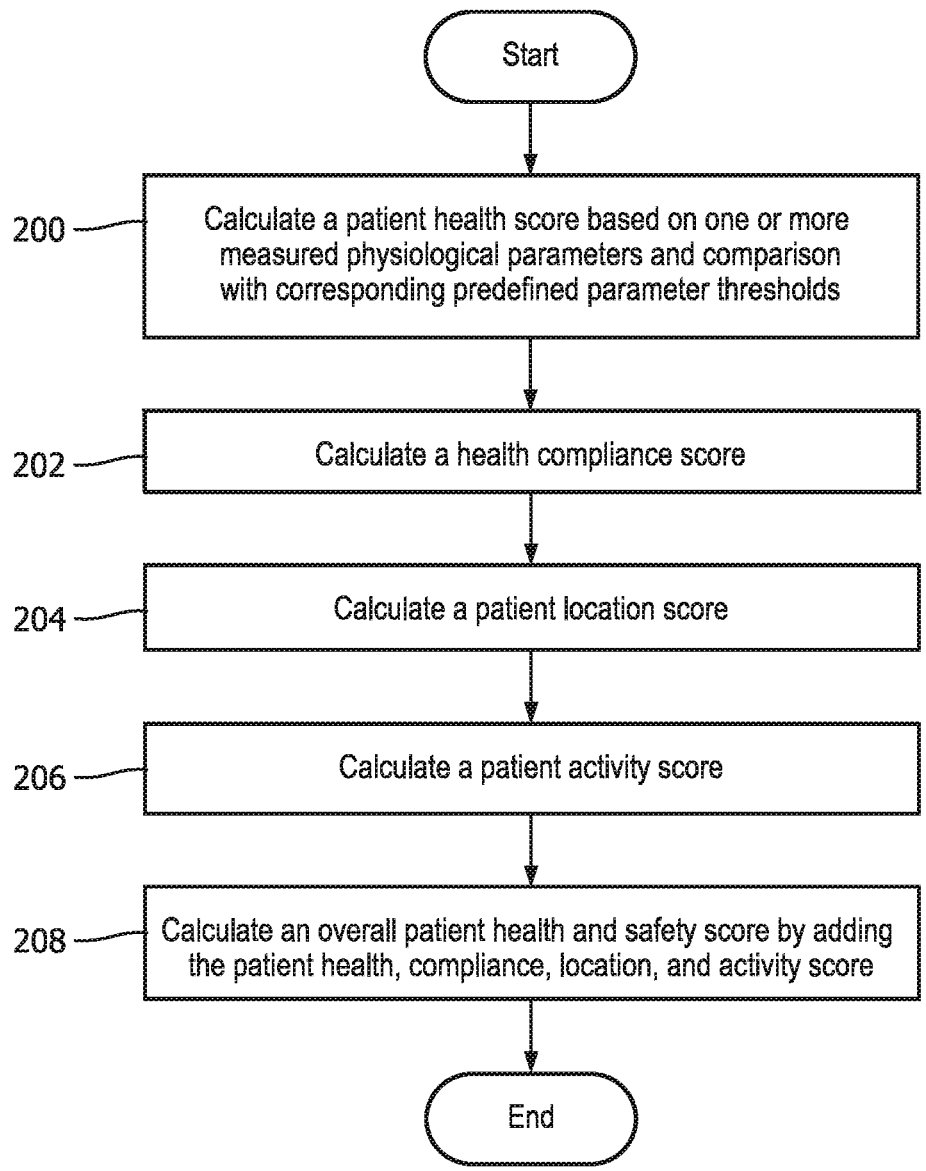
FIG. 2 is a flowchart illustrating an unweighted calculation of a total patient health and safety index or score.

FIG. 2 is a flowchart illustrating the calculation of an unweighted total patient health and safety index or score. The first step comprises calculating a patient health score based on one or more measured physiological parameters and comparison with corresponding predefined parameter thresholds (step 200). Following this, the monitoring system calculates a health compliance score (step 202), patient location score (step 204), and a patient activity score (step 206). An overall patient health and safety index or score is then calculated by summing all of the individual scores for the patient health, compliance, location, and activity (step 208).

Figure 3:
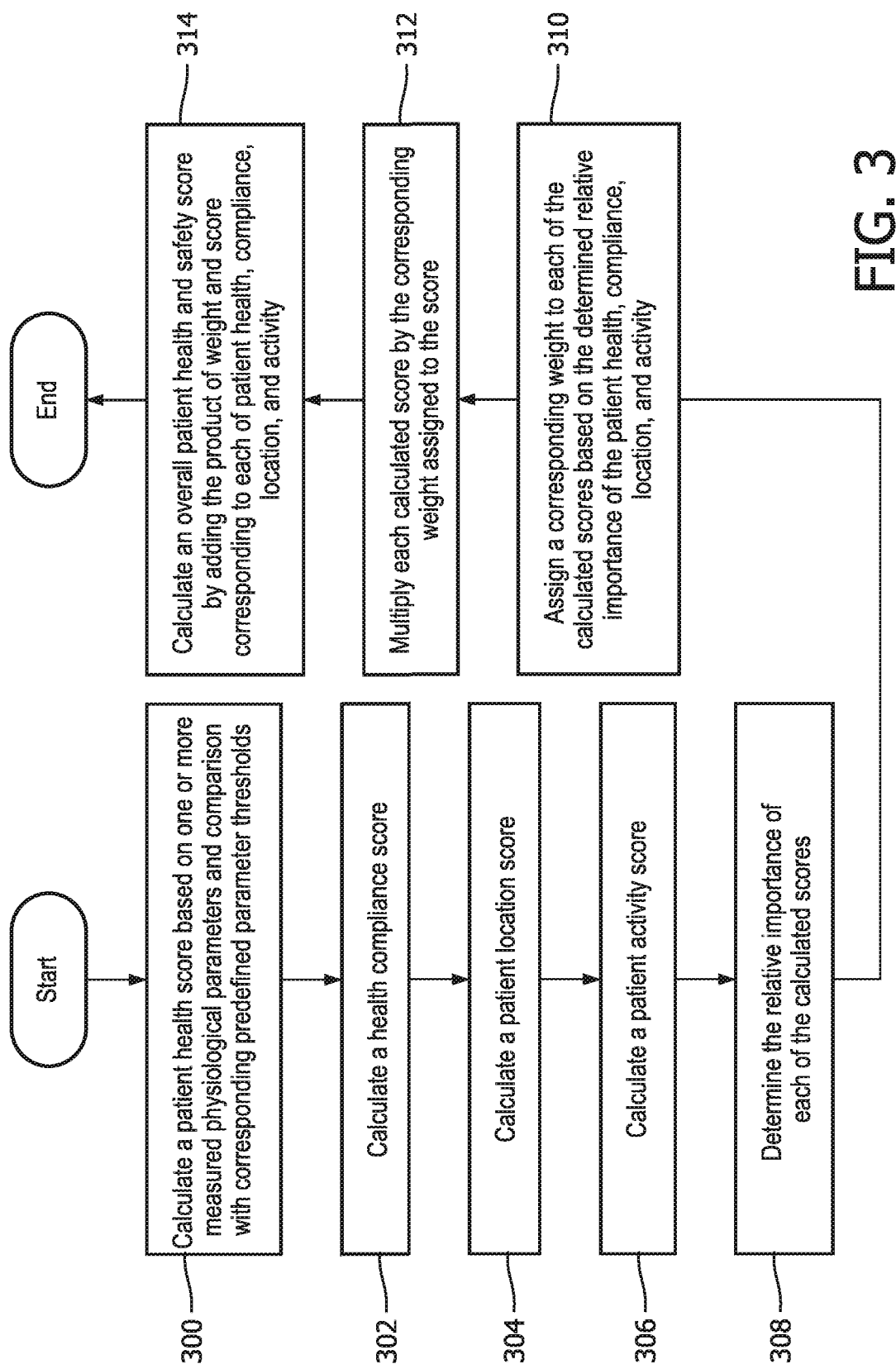
FIG. 3 is a flowchart illustrating a weighted calculation of a total patient health and safety index or score.

FIG. 3 is a flowchart illustrating the calculation of a weighted total patient health and safety index or score. The first step comprises calculating a patient health score based on one or more measured physiological parameters and comparison with corresponding predefined parameter thresholds (step 300). Following this, the monitoring system calculates a health compliance score (step 302), patient location score (step 304), and a patient activity score (step 306). After calculating each of the four individual scores, the system then determines the relative importance of each of the calculated scores (step 308). After determining the scores' relative importance, the monitoring system assigns a corresponding weight to each of the calculated scores based on the determined relative importance of the patient health, compliance, location, and activity (step 310). The system then multiplies each of the calculated scores by their corresponding weights (step 312). An overall patient health and safety score is computed by adding the product of weight and score corresponding to each of patient health, compliance, location, and activity (step 314).

In a preferred embodiment, the total patient health and safety index is calculated using the equation Total Score=$b_1x_1+b_2x_2+b_3x_3+b_4x_4$, where $b_i$ (i=1, 2, 3, 4) represent the weights of the various parameters $x_1$, $x_2$, $x_3$, and $x_4$ (e.g., $x_1$=location score, $x_2$=total compliance score, $x_3$=total health status index, $x_4$=activity score). For example, if the total compliance score $x_2$ and total health status index $x_3$ are considered more critical than the other two terms ($x_1$ and $x_4$) under the current patient context because the patient did not take his beta-blocker and the measured patient physiological parameters are somewhat higher than normal, then $b_2$ and $b_3$ are preferably assigned higher values than $b_1$ and $b_4$, e.g., $b_1$=0.2, $b_2$=0.3, $b_3$=0.3, and $b_4$=0.2. Thus, if $x_1$=+1, $x_2$=−1, $x_3$=−2, and $x_4$=+1, then the Total Score=(0.2)(+1)+(0.3)(−1)+(0.3)(−2)+(0.2)(+1)=−0.5. For this scoring system, a more negative Total Score means a greater likelihood that an alarm needs to be sent to one or more patient contact persons (which may be a family member, a case worker, a nurse, or a physician), depending on the preset alarm threshold. For example, if the preset alarm threshold for this type of situation is zero, then an alert will be sent to the appropriate alert recipients. But if the preset alarm threshold was initially set at −1.0, then no alert will be transmitted because the calculated weighted Total Score=−0.5 did not go below the preset alarm threshold.

In a preferred embodiment, a constant is added to a weighted sum of the individual terms corresponding to the user location score, user activity score, current health status, and user health score, wherein the constant represents a combined values or scores of the other parameters that remain unchanged regardless of variations in the patient's activities and locations (but which nonetheless remain essential to determine a user's overall health and safety context).

Figure 4:
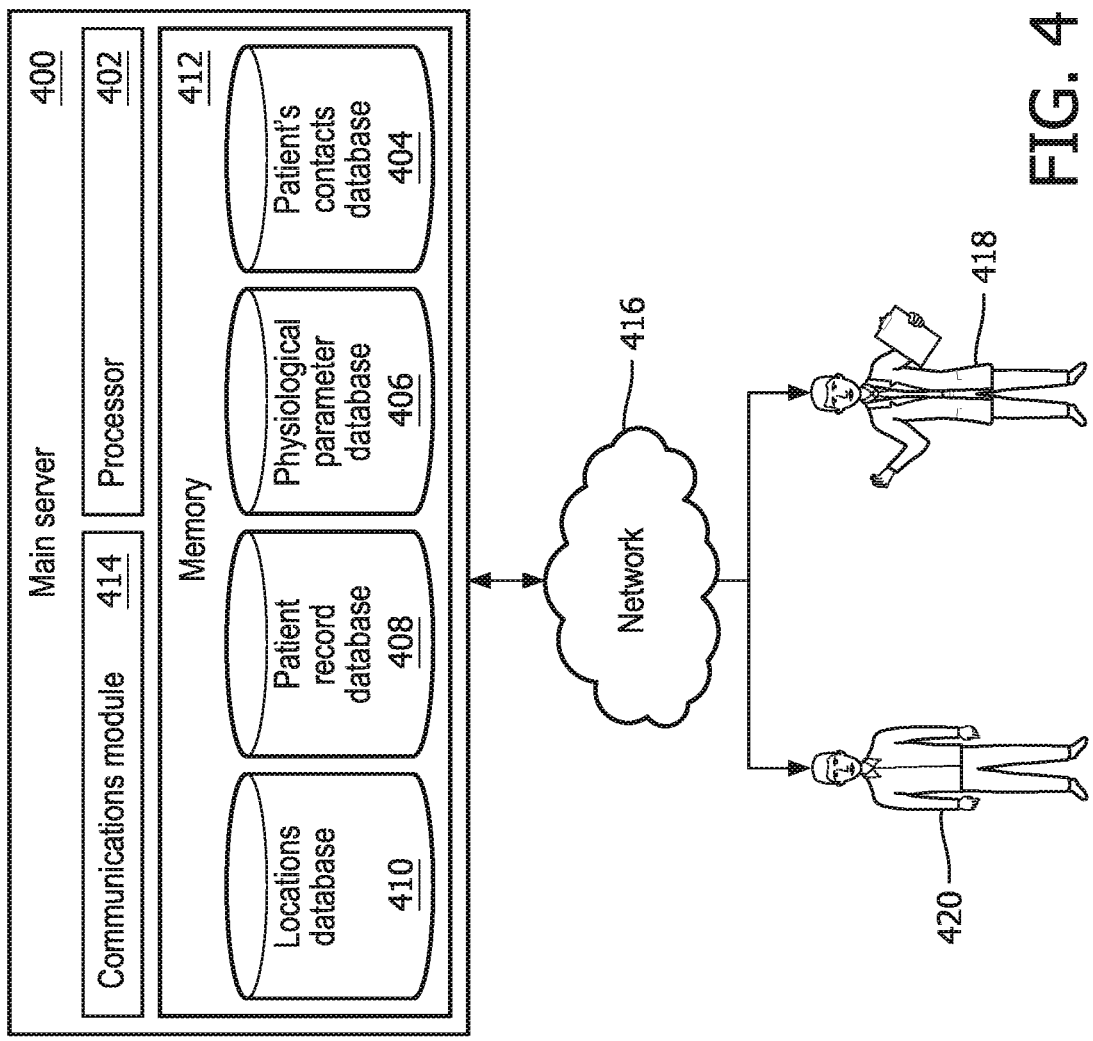
FIG. 4 is a block diagram of a monitoring system according to a preferred embodiment of the invention.

FIG. 4 is a block diagram of a monitoring system according to a preferred embodiment of the invention. The system comprises the multiparameter patient monitoring device 422 connected to at least one network server 400. The patient monitoring device 422 comprises a sensor module 424 that includes a heart rate sensor 426, motion sensor 428, temperature sensor 430, location tracker 432, and other sensors 434 such as a blood pressure monitor, oxygen saturation monitor, weight scale, temperature sensor, blood pressure sensor, respiratory sensor. Alternatively, each of the sensors may be separately housed. The patient monitoring device 422 also comprises a bus 436, processor 438, memory 440, communications module 442, graphical user interface 444, and power source 446. The patient monitoring device 422 is connected via the Internet, cloud, or a local network to at least one server 400 that houses several databases that include a locations database 410, patient record database 408, physiological parameter database 406, and patient's contacts database 404. The patient monitoring device 422 and the server 400 may be configured to allow access by at least one family member or relative 420 and a primary physician 418 via the Internet, cloud, or third-party service provider so that the relative 420 or primary physician 418 may input new data and delete or modify previously stored data.

The locations database 410 store data relating to various locations, facilities, residences, buildings (e.g., church, grocery stores, friends' houses, gym, clinic, hospital, barber shop, movie houses, etc.) that a patient frequently or regularly visits or is expected to visit, and all other nearby places or locations that are accessible to the patient, as well as default classifications (e.g., safe or unsafe) or initial or default scores for those location data. The patient record database 408 is where the patient's medical record are stored including the most recent required treatment protocol that the patient is undergoing, prescribed medications for the patient's one or more current medical conditions, preexisting conditions, known allergies, most recent medical diagnosis, previous diseases, vital signs measurements, etc. The patient monitoring device 422 stores patient physiological parameters (e.g., heart rate, blood pressure, and temperature) measured over a span of time into the physiological parameter database 406, etc. The patient's contacts database 404, on the other hand, contains contact information (e.g., home and office addresses, phone numbers, and relationship to patient) of the patient's family members, relatives, primary physician, therapist, friends, co-workers, etc. Preferably, other databases for storing other data such as the patient's calendar of activities, appointments, hospital visits, annual check-ups, dental visits, and travel plans are included in the main server 400.

Figure 5:
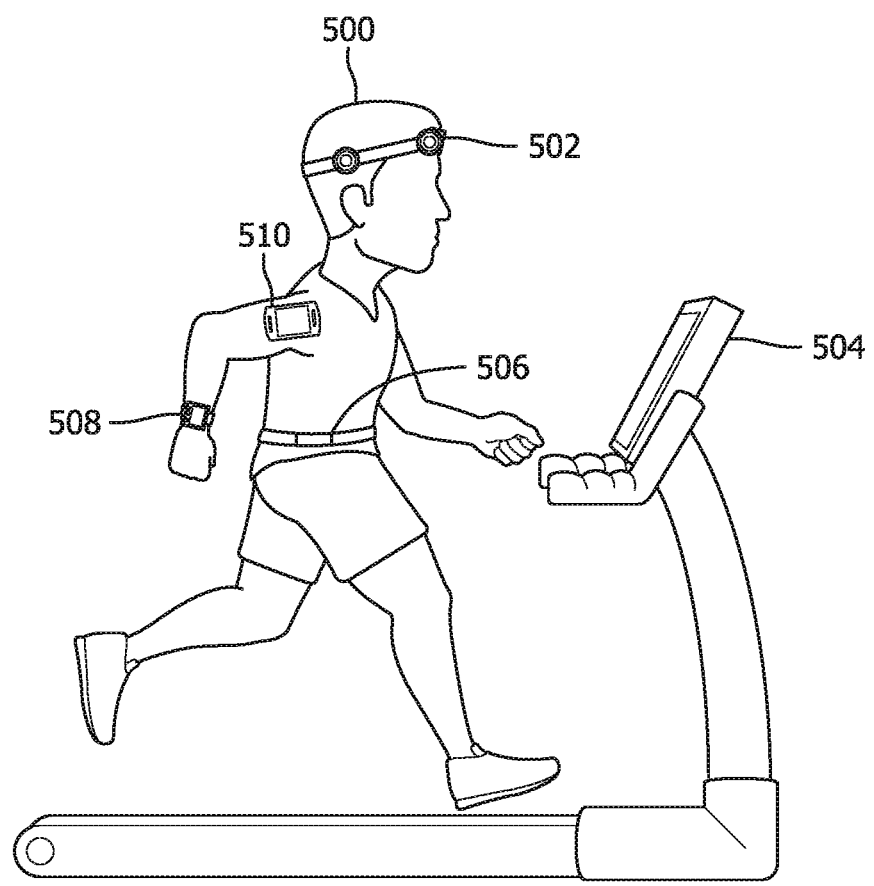
FIG. 5 shows a multiparameter monitoring system according to a preferred embodiment of the invention.

FIG. 5 shows a patient with a multiparameter monitoring system that comprises at least a mobile device 510, a heart rate sensor 508, motion sensor 506, and an imaging system 502. The mobile device 510 contains the patient monitoring software or application that manages communications between the mobile device 510 and the various sensors and devices. The mobile device 510 is preferably configured to receive data from the various sensors and transmit data to other devices and databases, as well as send instructions to the various sensors to collect data or perform physiological parameter measurements. The patient monitoring system preferably also includes an imaging system 502 to allow images of the patient's surroundings at a given location to be uploaded to one or more devices or servers. Using the imaging system 502, a family member or relative of the monitored patient may thus be able to remotely view in real-time the patient's present location and surrounding areas. This would be particularly useful in cases where the patient is determined to be in a new location unfamiliar or unknown to the patient's family members or relatives. By viewing the images in real time, the patient's relatives may be able to immediately gauge whether the patient is in a safe or unsafe location or setting and call for help if necessary. In a preferred embodiment, the images are later stored in the locations database for later closer inspection and location classification as safe or unsafe.

In a preferred embodiment of the invention, the scoring scheme used to calculate an overall patient health and safety context is a weighted scoring system that assigns appropriate weights for each of the contributing terms to the overall score, depending on each term's determined level of importance for a given set of patient's circumstances. The weighted scoring system provides a more accurate and reliable patient monitoring by assigning greater importance to certain terms (parameters or variables) that are more critical to the patient's health and safety than other parameters based on the patient's current circumstance. Thus, one parameter that was assigned the highest weight on a previous day may be assigned a relatively low weight the following day to reflect a change in the patient's circumstance.

For example, over the duration of a patient's required two-month weekly post-surgery hospital visitation, the patient's scheduled hospital visits is preferably assigned a relatively greater weight than other patient activities and locations (e.g., walk in a park) when calculating the patient's overall health and safety context score for that time or day. In another case, a patient has a scheduled hospital visit after lunch time, but began feeling dizzy and experiencing shortness of breath after having breakfast. His blood pressure monitor detects a higher than normal blood pressure and his heart rate monitor also indicates a higher than normal pulse rate. The monitoring system thus assigns greater weight to the currently-measured and analyzed patient's physiological parameters and the determined current patient health status compared to the weight previously assigned to the scheduled hospital visit. In this case, the monitoring system immediately contacts an emergency hotline and alerts the patient's primary physician and family members so the patient can be promptly attended to, even though the patient already has a scheduled hospital visit after lunch on that day.

Thus, in a preferred embodiment, when the system detects that the measured one or more critical patient physiological parameters (e.g., heart rate or blood pressure) exceed the corresponding one or more physiological parameter thresholds, the system ignores all other contributions to the overall health and safety score (e.g., scheduled activities and previously planned trips) and quickly sends an alert to one or more individuals or locations (e.g., hospitals, doctor's office, and home of a relative or family member). Thus, the system allows adjustments to previously assigned weights on previously-scheduled patient activities and locations (or the system simply ignores all other currently non-critical patient parameters) to allow the system to prioritize and quickly respond to unforeseen life-threatening patient situations or context.

In another example, a patient is detected to be non-compliant with at least one required health protocol (e.g., the patient failed to take his medicine for coronary heart disease) because the patient overslept and failed to hear an alert activated by one of the patient's monitoring sensors, e.g., a smart drug-dispensing system that can determine if a patient took his required medications on schedule. Upon determining that the patient was already fully awake and has failed to take his or medications according to the health protocol schedule, the monitoring system alerts the patient again to remind him or her to take his medications. The monitoring system also preferably immediately measures the patient's physiological parameters that include his heart rate and blood pressure. The monitoring system determines that the patient's physiological parameters all appear to be normal, the patient is detected to be walking around in a grocery store, but the patient still has not taken his medications. At a preset time or time intervals, the monitoring system calculates or assigns the appropriate scores for each of the detected patient activity (e.g., assign a score of "+1" when the patient is detected to be walking or sitting), determined patient location (e.g., assign also a "+1" when the patient is detected to be inside a favorite neighborhood grocery store), health protocol compliance (e.g., assign a score of "−1" for failing to take at least one of his medications), and measured and analyzed physiological parameters (e.g., assign a score of "+1" if the physiological parameters are all determined to be within normal ranges). In this case, a positive score, preferably one that exceeds a predefined threshold, means that the patient is in a safe environment and a sound state of health.

In one embodiment, the monitoring system is configured to monitor a patient and acquire new data to calculate a new patient overall health and safety context at predefined time intervals over a given period, e.g., every hour over a 24-hour period. The time intervals selected for monitoring may be changed by the monitoring system in cases where it determines that the patient needs a more frequent monitoring, e.g., the patient was non-compliant with a required health protocol and ignored repeated system reminders to comply. For example, the patient is taking several medications, as well as multi-vitamins, daily. If the patient failed to take his multi-vitamins, the monitoring system may be set to automatically assign a score of "−0.5" to that part of patient compliance because failing to take multi-vitamins would not be considered critical or life-threatening. But if a patient failed to take his statin, the monitoring system would preferably assign a score of "−1.0" for that aspect of patient compliance. On the other hand, if the patient failed to take his beta-blocker, which could potentially be life-threatening, the monitoring system would preferably set a more negative score, e.g., "−2.0," for that aspect of patient compliance. In a preferred embodiment, if the monitoring system determines that a patient's non-compliance is critical or potentially life threatening (e.g., the patient forgot to take his immunosuppressant following a kidney transplant), the monitoring system preferably not only sends out alerts to the primary physician and family members regarding the patient's non-compliance, but also immediately performs vital sign measurements using the monitoring system's one or more physiological sensors.

In a preferred embodiment, the patient's primary physician is authorized to modify the default score for at least the health compliance part of the patient monitoring, either manually during the patient's visit, or remotely. For example, the primary physician tentatively determines that the dizziness and skin rashes the patient was experiencing was due to the patient's reaction to the beta-blocker the patient was originally prescribed. The primary physician thus informs the patient to temporarily stop taking the beta-blocker for at least a day. The primary physician also promptly connects to the patient monitoring system wirelessly using her tablet and enters her username and password for the required authentication and authorization steps. Once inside the system, the physician manually resets the default setting for the beta-blocker compliance to a score of "0" temporarily until she has seen the patient the following day to do further tests to confirm her hunch about the patient's adverse reaction to the beta-blocker. Once the adverse reaction to the previous beta-blocker has been confirmed and a different beta-blocker prescribed to the patient, the default score of "−2.0" for beta-blocker non-compliance is preferably restored by the primary physician.

In another preferred embodiment, the method of the present invention further comprises using a learning algorithm to further enhance the accuracy and reliability of the overall user context analysis. The learning algorithm may be based on at least one learning models or approaches known in the art such as neural networks, Bayesian networks, deep learning, genetic algorithms, association rule learning, etc. The learning algorithm enables a multiparameter analysis of a patient's health and safety context that allows a sensible calculation, weighing, or prediction of the various variable's contribution to a total health and safety score that accurately reflects a user's changing patterns of activity, health parameter variations, and visited locations. A major benefit provided by a learning algorithm is that it minimizes the need for constant manual inputs by the one or more individuals involved in monitoring a patient. It also can enhance reliability and consistency in determining an overall patient health and safety context by minimizing subjective differences between manual inputs or score assignments made by different people.

The use of a learning algorithm is particularly useful when, for example, a user or patient is detected to be following a different pattern of activity from his or her previously detected activities or visited locations. For example, a patient may have been regularly seeing a primary physician over a period of months for regular check-ups after undergoing a surgery. The learning algorithm would thus detect a pattern of, say, weekly post-surgery visitations to a hospital by the user, and calculate a location and activity score and assign a weight to that location and activity that corresponds to a safe location (hospital) and a safe, expected, or recommended activity (doctor visitation). When the required post-surgery hospital visitations by the patient ends, the patient will engage in a new pattern of activity and visit old or new places, all of which the learning algorithm will detect.

In a preferred embodiment of the invention, a list of locations considered safe or unsafe are entered into a locations database, the inputting or updating of the location data being performed either by any one of the user, medical personnel, facility staff, family member, caretaker, or relative. In a preferred embodiment, the location database is updated as necessary either manually or through one or more learning algorithms, e.g., when a user visits a new location that was not previously stored in the locations database.

In a preferred embodiment, the system of the present invention automatically transmits the current location of a patient to one or more alert recipients (i.e., individuals to whom one or more alerts are to be sent) if the patient's current location is a previously undetected or unrecorded user location. Preferably, the patient's current location is sent to the alert recipients (e.g., primary physician, relative, family member, or caretaker) for classification by the at least one recipient as either safe or unsafe. For example, if a patient is detected to be in the vicinity of a deep lake or a neighborhood previously unvisited by the patient and also unlisted in the patient's locations database, the system will relay a message to an attending medical personnel, caretaker, relative, or family member to inform them about the patient's current location. Preferably, the system will also ask the one or more message recipients to assign a category for the newly-identified patient location, e.g., safe or unsafe. In a preferred embodiment, an identification or detection of a patient's current location as "unsafe" will automatically trigger the sending of an alert to an emergency hotline or a notification to one or more of the patient's contact persons listed in patient's contacts database.

The sensors may be virtually any sensor capable of sensing data about a user, the user's environment, the user's context, the state of various electronics associated with the user, etc. The sensors may include accelerometers, heart rate sensors, conductance sensors, optical sensors, temperature sensors, microphones, cameras, etc. These or other sensors may be useful for sensing, computing, estimating, or otherwise acquiring physiological parameters descriptive of the wearer such as, for example, steps taken, walking/running distance, standing hours, heart rate, respiratory rate, blood pressure, stress level, body temperature, calories burned, resting energy expenditure, active energy expenditure, height, weight, sleep metrics, etc.

The plurality of sensors used according to the present invention, in conjunction with a posture sensor, preferably include any combination of the following examples of sensors: activity sensor, inertial sensor, sleep sensor, sound sensor, camera, heart rate or pulse rate sensor, conductance sensor, optical sensor, temperature sensor, and other types of physiological sensors. Preferably, at least one inertial sensor is used to monitor the position of the user's spine and pelvis. The sensors can be placed in appropriate areas in the user body using adhesive strips or pads and other methods known in the art. Preferably, inertial sensors are placed at least on the user's lower back, upper back, and the pelvis area to allow measurement, for example, of the extent of forward, backward, or sideways bending performed by the user. In some embodiments, the sensors may share hardware in common with a user interface.

While many useful parameters may be obtained directly from the one or more sensors, other useful parameters are obtained by "extracting" them from other available data (including the sensor data). For example, raw accelerometer data may be processed to extract a number of steps taken, an estimate of calories burned, or an estimate of an activity being performed by the user (e.g., running, playing tennis, biking, etc.) Accordingly, various devices in the system may implement parameter extraction algorithms for processing available parameters (e.g., sensed parameters and other extracted parameters) to generate new parameters. In some embodiments, the sensors may implement such algorithms for parameter extraction in the same device as at least some of the sensors that obtain parameters upon which the algorithms depend or for parameter extraction that is local to the user though not necessarily in the same device as the predicate sensors. For example, in some embodiments, a wearable bracelet may report accelerometer data to a user's mobile device, which then applies an algorithm to estimate a number of steps taken using the accelerometer data. Additionally or alternatively, virtually any device may apply such parameter extraction algorithms, which in some cases may be provided as a service according to the systems and methods described herein. For example, the reporting framework, present invention, service application device, output device, or some other device (pictured or not pictured) may perform parameter extraction from input parameters available to the device. To the extent that such other devices may extract parameters that may be used as input to other services, such other devices may be considered sensors themselves. For example, a service application device that processes accelerometer data to estimate calories burned may also be considered a sensor that provides a calorie estimation for other services.

According to various embodiments described herein, sensors may be divided among two groups: direct reporting sensors and indirect reporting sensors. Direct reporting sensors may include any sensor that can be configured (e.g., by the present invention) to transmit parameters to other devices (e.g., the present invention or service application device). Such configuration may include adding a domain name or IP address to a configuration file of the direct reporting sensor to indicate a network location to which parameters should be transmitted. As an alternative, another device (e.g., the present invention) may periodically request that such parameters be reported. Various authentication and authorization may also be performed such as, for example, configuring the direct reporting sensor with information for confirming an identity (e.g., a password or public key) of the device to which parameters will be transmitted. In some embodiments, such configuration may require the user's manual approval.

Indirect reporting sensors, on the other hand, may only report parameters to predefined entities such as, for example, proprietary servers of the sensor manufacturer or a framework such as the AWS Internet of Things (IoT) cloud platform. Collectively, these other entities may be considered to constitute reporting frameworks. The reporting framework may provide an application programmer's interface (API) for allowing access to the parameters reported by the indirect reporting sensors (and, in some embodiments, parameters extracted by the reporting framework itself). Similar authentication and authorization measures may be taken with respect to the reporting framework and indirect reporting sensors as described above with respect to the direct reporting sensors. For example, the present invention may indicate to the reporting framework (via the API) an identification of the parameters which should be provided to the present invention along with a token indicating the user's approval for such sharing (or useful in obtaining such approval). Thereafter, the reporting framework may periodically or upon request transmit such parameters to the present invention (or other device such as a service application device).

As another example, the present invention may facilitate the transmission of parameters between devices by configuring one or more devices to establish communication among them without the present invention acting as an intermediary. For example, the present invention may provide an address of the service application device to the relevant sensors or reporting frameworks such that these devices may thereafter transmit parameters to the service application device. Additionally or alternatively, the present invention may provide the service application device with the address of the relevant sensors or reporting frameworks for polling. In some embodiments, configurations of any of these devices may also include providing authorization information such as, for example, an authorization token (e.g., an API token) generated by the present invention or other device for presentation upon transmission of parameters or a request for such a transmission.

Various approaches to enrolling a new sensor may be utilized by the sensor enrollment instructions. For example, in some embodiments, the sensor enrollment instructions may receive an identifier for a sensor from a consumer configuration device (e.g., as manually typed in by the user; captured by a camera via a barcode, QR code, or using optical character recognition; or received by the consumer configuration device via short-range communication such as NFC or Bluetooth) or directly from the sensor itself (e.g., as stored in memory at the time of manufacturing or registration with a reporting network). In some embodiments, the identifier may be or otherwise include a network address such as a MAC address or IP address. In some embodiments where the identifier is, at least in part, dynamic (e.g., an IP address), the sensor enrollment instructions may periodically re-execute to update the dynamic portion of the identifier. Upon receiving the identifier the sensor enrollment instructions may verify the device through communication with, for example, a reporting framework. Additionally, the sensor enrollment instructions may receive authorization in association with the device by, again, communicating with another device such as the reporting framework or the sensor itself.

The sensor may also be in the form of a wristwatch wearable device that includes an additional accelerometer as well as an optical sensor oriented toward the skin of a user to detect color changes. Pedometer instructions (which may have been installed on the mobile device by or in connection with the present invention) interpret the raw accelerometer data to output an estimation of the number of steps taken. Alternatively, the pedometer instructions of the mobile device may receive raw data from both accelerometers (e.g., as facilitated by the present invention) to give an improved estimation of steps taken. Heart rate instructions (which may have been installed on the mobile device by or in connection with the present invention) interpret the raw optical data to extract a heart rate parameter. The steps and heart rate parameters, as well as the raw accelerometer data, are provided to the proprietary wristwatch server for storage and further processing. The wristwatch wearable may not be configurable to share data with any other devices and, as such, may be considered an indirect reporting sensor.

The proprietary wristwatch server may be a server, blade, or VM operated, for example, by a manufacturer of the wristwatch wearable. Upon receiving parameters from the wristwatch wearable, they may be stored in a watch parameter storage and later used by activity identification instructions to identify a particular activity in which the user is engaged. For example, wristwatch accelerometer data may be used in conjunction with a trained model to distinguish playing tennis from kayaking. In some embodiments, the present invention may facilitate provision of additional input parameters (e.g., accelerometer data from the mobile device) to the proprietary wristwatch server to improve or activate operation of the parameter extraction algorithms or other services offered by the device manufacturer. The proprietary wristwatch server additionally includes an external access API for providing some or all of these parameters to the present invention or other devices.

An energy expenditure estimation service VM includes energy expenditure estimation instructions for executing a parameter extraction algorithm that estimates a number of calories burned from various inputs. Similarly a fitness coaching service VM includes fitness coaching instructions for processing various input data to provide coaching messages to the user.

The device of the present invention preferably includes a processor, cache/system memory, user interface, network interface, and storage, and for some devices, sensors interconnected via one or more system buses.

The processor may be any hardware device capable of executing instructions stored in memory or storage or otherwise processing data. As such, the processor may include a microprocessor, field programmable gate array (FPGA), application-specific integrated circuit (ASIC), or other similar devices. In some embodiments, such as those relying on one or more ASICs, the functionality described as being provided in part via software may instead be hardwired into the operation of the ASICs and, as such, the associated software may be omitted.

The cache/system memory may include various memories such as, for example L1, L2, or L3 cache or system memory. As such, the memory may include static random access memory (SRAM), dynamic RAM (DRAM), flash memory, read only memory (ROM), or other similar memory devices.

The communication interface may include one or more devices for enabling communication with other hardware devices. For example, the network interface may include a network interface card (NIC) configured to communicate according to the Ethernet protocol. Additionally, the communication interface may implement a TCP/IP stack for communication according to the TCP/IP protocols. Various alternative or additional hardware or configurations for the communication interface will be apparent. In some embodiments, the communication interface may include an NFC, Bluetooth, or other short range wireless interface. Various alternative or additional hardware or configurations for the communication interface will be apparent.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. For example, the storage may store an operating system for controlling various basic operations of the hardware.

Where the device implements a sensor, the storage may also include sensor polling instructions for periodically on the acquisition of new data, polling the sensors for new raw data. The storage may also include parameter extraction algorithm application instructions for executing one or more parameter extraction algorithms to extract additional parameters from the parameters obtained by the sensor polling instructions, other parameter extraction algorithms, or from other devices. In some embodiments, the set of parameter extraction algorithms may be supplemented by addition of new algorithms (e.g., as a result of subscribing to a new service). To enable such extension of functionality, the parameter extraction algorithm application instructions are adapted to call each of the parameter extraction algorithms during run-time. For example, in some embodiments, the parameter extraction algorithms may be written using an interpreted code (e.g., JAVA™ or a proprietary device code) while the parameter extraction algorithm application instructions include or invoke an appropriate interpretation engine (e.g., JAVA™ runtime environment or other interpreter). As another example, the parameter extraction algorithms may instead be compiled code while the parameter extraction algorithm application instructions may include code that calls each parameter extraction algorithm in turn. In some embodiments, the extraction algorithm application instructions may be as simple as code that calls each parameter extraction algorithm in sequence. Various additional organizations for expanding algorithm-based functionality will be apparent.

The storage may also include parameter reporting instructions for transmitting parameters sensed by the sensor polling instructions or extracted by the parameter extraction algorithms. For example, where the sensor is an indirect reporting sensor, the parameter reporting instructions may cause the processor to transmit parameters to a reporting framework. Where the sensor is a direct reporting sensor, the parameter reporting instructions may cause the processor to transmit parameters to one or more device identified or authorized in the parameter reporting configurations. The parameter reporting instructions may operate periodically, upon the acquisition of new parameters, or upon receiving a pull request from another device.

In some embodiments, such as those wherein the sensor provides some output of at least the locally gathered or extracted parameters, the storage also includes parameter output instructions for causing display or other output of parameters, for example, upon request by the user. In embodiments wherein the sensor is also a output device, the parameter output instructions may additionally effect output of parameters or other information received from other devices via the remote parameter receipt instructions. Such remote parameter receipt instructions may operate periodically, upon request by the user (e.g., to sync with service providers or to display a parameter that is remotely obtained), or upon indication from the remote device of the availability of such parameters to request, receive, interpret, store, or otherwise process remote parameters.

It will be apparent that various information described as stored in the storage may be additionally or alternatively stored in the memory. In this respect, the memory may also be considered to constitute a "storage device" and the storage may be considered a "memory." Various other arrangements will be apparent. Further, the memory and storage may both be considered to be "non-transitory machine-readable media." As used herein, the term "non-transitory" will be understood to exclude transitory signals but to include all forms of storage, including both volatile and non-volatile memories.

While the device is shown as including one of each described component, the various components may be duplicated in various embodiments. For example, the processor may include multiple microprocessors that are configured to independently execute the methods described herein or are configured to perform steps or subroutines of the methods described herein such that the multiple processors cooperate to achieve the functionality described herein. Further, where the device is implemented in a cloud computing system, the various hardware components may belong to separate physical systems. For example, the processor may include a first processor in a first server and a second processor in a second server.

The user profile also includes a sensors record set for describing the sensors enrolled for the user. The sensors record set includes an input id field for identifying an enrolled sensor (e.g., a user-provided name, an identifier generated by the present invention, an identifier used by another device such as a reporting framework, or a globally unique identifier), an input types field for identifying (e.g., using the same parameter type taxonomy used by the service provider to specify inputs and outputs to a service) input parameters available from the sensor, and indirect field for identifying whether a sensor is a direct reporting or indirect reporting sensor, and an authorization token field for storing one or more tokens (e.g., encryption keys, passwords, API tokens, etc.) needed for accessing the data from the sensor. It will be apparent that additional or alternative information about each sensor may be provided by the sensors record set such as, for example, one or more network addresses of the sensor, one or more network addresses of a reporting framework, an indication of whether the present invention must act as an intermediary to other services (e.g., between the service application device and a direct reporting sensor or reporting framework)

As an example, a first record indicates that a device is able to provide two input types: pocket-carried pedometer and pocket-carried accelerometer data. This information is directly reported by the sensor and is not associated with any authorization tokens. In various embodiments, the record may correspond to the mobile device.

A second example record indicates that a device provides three input parameter types: wrist-worn pedometer, wrist-worn accelerometer, and activity data. This information is only obtainable from a reporting framework associated with the device using the defined authorization token. In various embodiments, the second record may correspond to the wristwatch wearable or proprietary wristwatch server. This record identifies input parameters available from two different sensors: the wristwatch wearable creates the accelerometer and pedometer data, while the proprietary wristwatch server extracts the activity data. For the purposes of sharing or for the purposes of user presentation, however, these two sensors may be collapsed into a single "device" record because all three parameters will be obtained from the reporting framework (due to indirect reporting) or because the user may consider the complete solution offered by the manufacturer (device and reporting framework) to constitute a single device which they purchased and use.

The present invention is not intended to be restricted to the several exemplary embodiments of the invention described above. Other variations that may be envisioned by those skilled in the art are intended to fall within the disclosure.

What is claimed is:

1. A medical alert method for creating a multidimensional user context analysis comprising:
    providing a patient monitoring device comprising one or more physiological sensors, a motion sensor, a location tracker, a processor, a wireless communications interface, a memory device, a graphical user interface, and a power source, wherein the patient monitoring device is configured to be carried by a user;
    acquiring the user's most recently assigned health protocol and the user's current location;
    monitoring, via the patient monitoring device, user compliance to the user's most recently assigned health protocol;
    computing a health compliance score based on the monitored user compliance to the user's most recently assigned health protocol;
    computing a location score using the user's current location measured by the patient monitoring device, the user's historical activity record measured by the patient monitoring device, frequently-visited places measured by the patient monitoring device, and one or more scheduled user activities, wherein computing the location score is based on determining whether the user's current location is an identified safe location, an identified unsafe location, or an unidentified new location;
    computing an overall user health score based on the computed health compliance score, and the computed location score; and
    sending an alert message to a physician or a caretaker after the computed overall health score violates a predefined threshold, wherein the alert message includes the user's current location, a reason for the alert, and a request for the physician or the caretaker to provide an indication of whether the user's current location is safe or unsafe when the user's current location is the unidentified new location.

2. The medical alert method as recited in claim 1, wherein the method further comprises:
    acquiring one or more preset physiological parameter thresholds;
    measuring the user's one or more physiological parameters;
    comparing the user's one or more physiological parameters with the corresponding one or more preset physiological parameter thresholds; and
    calculating a user health index based on the measured one or more physiological parameters and comparison with the corresponding one or more preset physiological parameter thresholds.

3. The medical alert method as recited in claim 2, wherein the user's one or more physiological parameters comprise heart rate, blood pressure, oxygen saturation, respiration, activity, weight, and temperature.

4. The medical alert method as recited in claim 3, wherein the method further comprises:
   acquiring a list of the frequently-visited places, and a list of the one or more scheduled user activities; and
   calculating a user activity score based on at least one of the user's historical activity record, medical record, the list of the frequently-visited places, the user's current location, or the list of the one or more scheduled user activities.

5. The medical alert method as recited in claim 4, wherein the overall user health score is further based on the calculated user health index and the calculated user activity score.

6. The medical alert method as recited in claim 4, wherein the overall user health score is calculated as follows: overall user health score=$b1 \times 1 + b2 \times 2 + b3 \times 3 + b4 \times 4$ wherein, $b1$=Computed health compliance score, $x1$=Computed health compliance score weighting factor, $b2$=Calculated user health index, $x2$=Calculated user health index weighting factor, $b3$=Calculated activity score, $x3$=Calculated activity score weighting factor, $b4$=Computed location score, and $x4$=Computed location score weighting factor.

7. The medical alert method of claim 1, wherein a patient's primary physician is authorized to remotely modify a default score for the health compliance score.

8. The medical alert method of claim 1, wherein the patient monitoring device is configured to send an alert to an emergency hotline after identification of the user's current location as unsafe.

9. The medical alert method of claim 1, wherein the patient monitoring device is a wearable device.

10. The medical alert method of claim 9, wherein the wearable device further comprises a wristwatch server.

11. A medical alert system for creating a multidimensional user context analysis comprising:
   a main server comprising a first processor and a first memory, a patient records database, and a locations database, wherein the patient records database include a user's most recently assigned health protocol;
   a patient monitoring device, comprising one or more physiological sensors, a motion sensor, a location tracker, a second processor, a wireless communications interface, a second memory, a graphical user interface, and a power source, wherein the patient monitoring device is configured to be carried by a user and monitor compliance of the user;
   a network interconnecting the patient monitoring device with the main server, wherein the main server is configured to
      compute a health compliance score based on the monitored compliance and the user's most recently assigned health protocol,
      compute a location score based on the user's current location measured by the patient monitoring device, the user's historical activity record measured by the patient monitoring device, frequently-visited places measured by the patient monitoring device, and one or more scheduled user activities, wherein computing the location score is based on determining whether the user's current location is an identified safe location, an identified unsafe location, or an unidentified new location,
      compute an overall user health score based on the health compliance score and the computed location score, and
      send an alert message to a physician or a caretaker after the computed overall user health score violates a predefined threshold, wherein the alert message includes the user's current location, a reason for the alert, and a request for the physician or the caretaker to provide an indication of whether the user's current location is safe or unsafe when the user's current location is the unidentified new location.

12. The medical alert system as recited in claim 11, wherein the main server is further configured to calculate an activity score based on the user's historical activity record, medical record, the frequently-visited places, the user's current location, and the one or more scheduled user activities.

13. The medical alert system as recited in claim 11, wherein the main server further comprises:
   a physiological parameter database comprising one or more of heart rate, blood pressure, oxygen saturation, respiration, activity, weight, and temperature.

14. The medical alert system as recited in claim 13, wherein the physiological parameter database comprises one or more physiological parameter thresholds, and wherein the main server is configured to calculate a user health index based on the measured one or more physiological parameters and comparison with the corresponding one or more physiological parameter thresholds.

15. The medical alert system as recited in claim 14, wherein the locations database includes one or more of the user's historical activity record, medical record, the frequently-visited places, the user's current location, or the one or more scheduled user activities; and the main server is configured to
   calculate a user activity score based on at least one of the user's historical activity record, the medical record, the frequently-visited places, the user's current location, or the one or more scheduled user activities.

16. The medical alert system as recited in claim 15, wherein the overall user health score is further based on the calculated user health index and the calculated user activity score.

17. The medical alert system as recited in claim 16, wherein the overall user health score is calculated as follows: overall user health score-$b1 \times 1 + b2 \times 2 + b3 \times 3 + b4 \times 4$ wherein, $b1$=Computed health compliance score, $x1$=Computed health compliance score weighting factor, $b2$=Calculated user health index, $x2$=Calculated user health index weighting factor, $b3$=Calculated activity score, $x3$=Calculated activity score weighting factor, $b4$=Computed location score, and $x4$=Computed location score weighting factor.

18. A medical alert method for monitoring patient activity, location, and health protocol compliance using a multidimensional context analysis comprising:
   providing a patient monitoring device comprising one or more physiological sensors, a motion sensor, a location tracker, a processor, a wireless communications interface, a memory device, a graphical user interface, and a power source, wherein the patient monitoring device is configured to be carried by a user;
   acquiring the user's most-recently assigned health protocol, the user's historical activity record, medical record, frequently-visited places, tile user's current location, and one or more scheduled user activities;
   monitoring, via the patient monitoring device, user compliance to the acquired user's most-recently assigned health protocol;
   computing a health compliance score based on the monitored user compliance to the acquired user's most-recently assigned health protocol;

measuring the user's one or more physiological parameters;

comparing the measured user's one or more physiological parameters with corresponding one or more preset physiological parameter thresholds;

calculating a user health index based on the measured one or more physiological parameters and comparison with the corresponding one or more preset physiological parameter thresholds;

computing a location score calculated using the user's current location measured by the patient monitoring device, the user's historical activity record measured by the patient monitoring device, the frequently-visited places measured by the patient monitoring device, and the one or more scheduled user activities, wherein computing the location score is based on determining whether the user's current location is an identified safe location, an identified unsafe location, or an unidentified new location;

calculating a user activity score based on at least one of the user's historical activity record, the medical record, the frequently-visited places, the user's current location, and one or more of the scheduled user activities;

computing an overall user health score based on the computed health compliance score, the calculated user health index, the calculated activity score, and the computed location score; and sending an alert message to a physician or a caretaker after the computed overall user health score violates a predefined threshold, wherein the alert message includes the user's current location, a reason for the alert, and a request, for the physician or the caretaker to provide an indication of whether the user's current location is safe or unsafe when the user's current location is the unidentified new location.

* * * * *